United States Patent [19]

Smith

[11] Patent Number: 4,914,250

[45] Date of Patent: Apr. 3, 1990

[54] COUPLING PROCESS

[75] Inventor: R. Scott Smith, Baton Rouge, La.

[73] Assignee: Ethyl Corporation, Richmond, Va.

[21] Appl. No.: 356,185

[22] Filed: May 24, 1989

Related U.S. Application Data

[63] Continuation-in-part of Ser. No. 207,959, Jun. 17, 1988, abandoned.

[51] Int. Cl.$^4$ ............................................. C07C 2/64
[52] U.S. Cl. ..................................... 585/452; 585/453
[58] Field of Search ................................. 585/452, 453

[56] References Cited

U.S. PATENT DOCUMENTS 4,179,471 12/1979 Cobb et al. .......................... 585/411
4,620,056 10/1986 Shimizu et al. ...................... 585/453

Primary Examiner—Curtis R. Davis
Attorney, Agent, or Firm—Patricia J. Hogan

[57] ABSTRACT

An alkene selected from ethene, propene, and mixtures thereof is coupled with an aromatic hydrocarbon having an active hydrogen on a saturated alpha-carbon in the presence of a supported potassium or potassium alloy as a catalyst and sodium hydroxide, potassium hydroxide, or a mixture thereof as a co-catalyst. In preferred embodiments of the invention, the active hydrogen-containing aromatic hydrocarbon is an alkylbenzene, such as toluene; and the co-catalyst is a hydroxide or hydroxide mixture formed in situ by adding water to the potassium or potassium alloy.

16 Claims, No Drawings

COUPLING PROCESS

CROSS REFERENCE TO RELATED APPLICATION

This application is a continuation-in-part of copending application Ser. No. 207,959, filed June 17, 1988, and now abandoned.

FIELD OF INVENTION

This invention relates to a process for coupling ethene and/or propene with an aromatic hydrocarbon having an active hydrogen on a saturated alpha-carbon.

BACKGROUND

As disclosed, e.g., in U.S. Pat. Nos. 3,244,758 (Eberhardt) and 4,179,580 (Cobb) and in European Patent 128001 (Kudoh et al.), it is known that supported alkali metals, including potassium and sodium-potassium alloys, are useful as catalysts in the coupling of ethylenically-unsaturated hydrocarbons with aromatic hydrocarbons having an active hydrogen on a saturated alpha-carbon. The supported alkali metals are more effective than the corresponding unsupported alkali metals in such reactions but are still not as effective as might be desired.

U.S. Pat. No. 4,620,056 (Shimizu et al.) teaches that the catalytic activity of unsupported sodium metal in such coupling reactions can be increased by conducting the reactions in the presence of a combination of a styrene-type compound and a potassium compound, such as potassium hydroxide, as co-catalysts.

Pines et al., *Journal of the American Chemical Society*, Vol. 80, pp. 6001–6004 (1958) disclose the use of sodium hydroxide as a promoter for the sodium-catalyzed side chain aralkylation of alkylbenzenes with styrene.

SUMMARY OF INVENTION

An object of this invention is to provide a novel process for coupling ethene and/or propene with an aromatic hydrocarbon having an active hydrogen on a saturated alpha-carbon.

Another object is to provide such a process which utilizes a supported alkali metal as a catalyst.

A further object is to provide such a process in which the reaction rate and product yield are increased.

These and other objects are attained by coupling ethene and/or propene with an aromatic hydrocarbon having an active hydrogen on a saturated alpha-carbon in the presence of a supported potassium or potassium alloy as a catalyst and sodium hydroxide, potassium hydroxide, or a mixture thereof as a co-catalyst, the catalyst composition containing about 200–1500 weight % of support and about 4–40 mol % of co-catalyst, based on the amount of alkali metal catalyst.

DETAILED DESCRIPTION

As already mentioned, the alkene which is coupled with the aromatic hydrocarbon in the practice of the invention may be ethene, propene, or a mixture thereof. However, it is preferably propene or a propene-ethene mixture.

The aromatic hydrocarbon having an active hydrogen on a saturated alpha-carbon may be any such compound that is known to be useful in such reactions, such as toluene, ethylbenzene, n-propylbenzene, isopropylbenzene, n-butylbenzene, sec-butylbenzene, isobutylbenzene, n-eicosylbenzene, o-, m-, and p-xylenes, o-, m-, and p-ethyltoluenes, 1,3,5-trimethylbenzene, 1,2,4,5- and 1,2,3,5-tetramethylbenzenes, p-diisopropylbenzene, 1- and 2-methylnaphthalenes, dimethylnaphthalenes, 1-ethyl-4-n-octadecylnaphthalene, 1,4-di-n-pentylnaphthalene, 1,2,3,4-tetrahydronaphthalene, indan, cyclohexylbenzene, methylcyclohexylbenzene, diphenylmethane, etc. However, it is generally a hydrocarbon corresponding to the formula $RR'R''CH$, in which R is an aryl group of up to 20 carbons and R' and R'' are independently selected from hydrogen and alkyl and aryl groups of up to 20 carbons; and it is apt preferably to be an alkylbenzene having one or more ar-alkyl groups. A particularly preferred aromatic hydrocarbon is toluene.

The mol ratio of alkene to aromatic hydrocarbon varies with the particular reactants employed and the products desired, particularly since the aromatic hydrocarbon may have one or more active hydrogens, and it may be desired to react the alkene with only one or with more than one active hydrogen in the aromatic hydrocarbon. It is frequently preferred to employ the reactants in the stoichiometric amounts appropriate for the preparation of the desired product. However, either reactant can be used in excess.

The alkali metal employed as a catalyst may be potassium or a potassium alloy, e.g., a sodium-potassium alloy having a potassium content of 40–90% by weight. As in Cobb, the teachings of which are incorporated herein in toto by reference, it appropriately has its surface area increased by being finely divided or liquid as well as by being supported on any suitable support material, such as diatomaceous earth, activated charcoal, granular coke, silica, alumina, pumice, porcelain, quartz, steel turnings, copper shot, sodium carbonate, potassium carbonate, etc. The amount of alkali metal used is a catalytic amount, generally about 2–10 mol %, based on the amount of either of the reactants when they are employed in equimolar amounts or on the amount of the major reactant when they are not utilized in equimolar amounts.

The co-catalyst of the invention is sodium hydroxide, potassium hydroxide, or a mixture thereof. Like the alkali metal, it is used in finely divided form; and it may be incorporated into the reaction mixture as the hydroxide, or it may be generated in situ by reacting water with the supported catalyst.

The reaction is conducted by heating a mixture of the alkene, the active hydrogen-containing aromatic hydrocarbon, the supported catalyst, and the co-catalyst under substantially anhydrous conditions at a suitable temperature, generally about 100°–300° C., preferably about 175°–200° C., to couple the reactants. It is generally conducted in the absence of a diluent or in the presence of an excess of the active hydrogen-containing aromatic hydrocarbon as the sole diluent. However, an inert diluent can be used if desired. Exemplary of such diluents are liquid alkanes, cycloalkanes, and aromatic hydrocarbons, such as pentane, hexane, isooctane, cyclohexane, naphthalene, decahydronaphthalene, white oils, etc.

When the co-catalyst is to be generated in situ, it is preferred to heat a mixture of the aromatic hydrocarbon and the supported catalyst to the reaction temperature prior to adding water in order to shorten the induction period that sometimes follows the subsequent addition of the alkene.

The process of the invention proceeds at a faster rate and provides higher product yields with fewer by-products than comparable processes conducted in the absence of the co-catalyst, and it is particularly advantageous as a means of alkylating alkylaromatic compounds, especially alkylbenzenes, to form compounds useful as solvents, internal standards, intermediates for polymers, pharmaceuticals, or pesticides, etc.

The extent to which the use of both the support and the co-catalyst increases the activity of the potassium or potassium alloy catalyst is surprising. Comparison of experiments in which both the support and the co-catalyst were employed with experiments in which neither was used, experiments in which only the support was utilized, and experiments in which only the co-catalyst was utilized demonstrate that the support and co-catalyst act synergistically to provide an increase in caatalytic activity that is greater than the additive effect that might have been expected from the results achieved by the use of the supports and co-catalysts separately.

The following examples are given to illustrate the invention and are not intended as a limitation thereof.

COMPARATIVE EXAMPLE A

A suitable reaction vessel was charged with 4.9 g of diatomaceous earth, 92 g (1.0 mol) of dry toluene, $C_{11}$ paraffin as a GC standard, and 1.0 g of potassium. The mixture was stirred and heated AT 190° C. for one hour, after which the temperature was lowered to 185° C. and propene was charged until a pressure of 2758 kPa was reached; and the propene pressure was then maintained at 2689–2758 kPa throughout the reaction. Periodically the stirrer was stopped to allow the solids to settle; and samples were drawn, allowed to cool to room temperature, and subjected to GC analysis to determine the amounts of unreacted toluene, desired isobutylbenzene (IBB) product, and n-butylbenzene (NBB), methylindan (MI), and methylpentene (MP) by-products. Finally the reaction was stopped by cooling the reactor to 75° C., venting most of the propene, and injecting 10 mL of methanol under nitrogen pressure to quench the catalyst. The results of the analyses are shown below.

| Time (min.) | Mols × 100 | | | | |
|---|---|---|---|---|---|
| | Toluene | IBB | NBB | MI | MP |
| 0 | 100 | 0 | 0 | 0 | 0 |
| 40 | 83.0 | 10.0 | 0.42 | 2.60 | 1.0 |
| 80 | 74.2 | 16.7 | 0.73 | 4.05 | 1.8 |
| 120 | 66.8 | 22.0 | 0.94 | 4.97 | 2.5 |
| 160 | 61.2 | 25.1 | 1.09 | 5.45 | 3.3 |
| 200 | 59.0 | 26.9 | 1.11 | 5.72 | 3.4 |

COMPARATIVE EXAMPLE B

Comparative Example A was repeated except that a portion of the dry toluene was replaced with toluene containing 565 ppm of water so as to provide 0.31 mmol of water in the reaction mixture, and the amount of potassium was increased to 1.02 g (26.1 mmols) to compensate for the amount of potassium that would react with the water. Thus, the reaction mixture contained about 1.2 mol % of co-catalyst, based on the amount of catalyst. The analytical results are shown below.

| Time (min.) | Mols × 100 | | | | |
|---|---|---|---|---|---|
| | Toluene | IBB | NBB | MI | MP |
| 0 | 100 | 0 | 0 | 0 | 0 |
| 40 | 83.2 | 8.1 | 0.57 | 0.81 | 0.9 |
| 80 | 68.7 | 22.1 | 1.33 | 2.68 | 2.6 |
| 120 | 60.9 | 29.1 | 1.70 | 3.41 | 3.8 |
| 160 | 52.9 | 35.2 | 1.99 | 4.22 | 3.9 |
| 200 | 48.7 | 38.1 | 2.09 | 4.40 | 4.9 |

As demonstrated in the preceding examples, some increases in reaction rate and product yield are achieved by the use of very small amounts of water in the reaction mixture. The following example shows that greater improvements are effected by the use of an amount of water within the scope of the present invention.

EXAMPLE I

Comparative Example B was repeated except that the amount of water in the reaction mixture was increased to 2.9 mmols and the amount of potassium was increased to 1.22 g (31.2 mmols). Thus, the reaction mixture contained about 10.2 mol % of co-catalyst, based on the amount of catalyst. The analytical results are shown below.

| Time (min.) | Mols × 100 | | | | |
|---|---|---|---|---|---|
| | Toluene | IBB | NBB | MI | MP |
| 0 | 100 | 0 | 0 | 0 | 0 |
| 40 | 91.3 | 4.1 | 0.41 | 0 | 0.6 |
| 80 | 74.2 | 18.8 | 2.00 | 0.12 | 2.2 |
| 120 | 56.9 | 37.1 | 3.99 | 0.27 | 5.0 |
| 160 | 39.9 | 52.8 | 5.21 | 0.44 | 7.4 |
| 200 | 26.9 | 64.8 | 5.90 | 0.58 | 12.6 |

EXAMPLE II

Comparative Example A was essentially repeated except that there was no preheating at 190° C. and the 1.0 g of potassium was replaced with 1.9 g of NaK (an alloy having a K content of 78% by weight) and 8.6 mmols of water were charged to the reaction vessel before heating was begun. The analytical results are shown below.

| Time (min.) | Mols × 100 | | | | |
|---|---|---|---|---|---|
| | Toluene | IBB | NBB | MI | MP |
| 0 | 100 | 0 | 0 | 0 | 0 |
| 40 | no samples taken - no propene uptake | | | | |
| 120 | no samples taken - no propene uptake | | | | |
| 160 | 98.3 | 1.4 | 0.14 | 0 | 0.1 |
| 200 | 84.1 | 12.6 | 1.65 | 0.23 | 2.0 |
| 240 | 62.3 | 33.5 | 4.06 | 0.58 | 3.5 |
| 280 | 30.4 | 53.7 | 5.94 | 0.76 | 5.4 |
| 320 | 19.5 | 64.2 | 6.56 | 0.80 | 8.7 |
| 360 | 13.0 | 70.0 | 6.54 | 0.7d | 1.7 |

EXAMPLE III

Example II was repeated except that the water was not added until the mixture of diatomaceous earth, toluene, paraffin, and NaK had been heated to 185° C. The analytical results are shown below.

| Time  | Mols 33 100 | | | | |
|-------|---------|------|------|------|------|
| (min.) | Toluene | IBB | NBB | MI | MP |
| 0 | 100 | 0 | 0 | 0 | 0 |
| 40 | 100 | 0 | 0 | 0 | 0 |
| 80 | 100 | 0 | 0 | 0 | 0 |
| 120 | 89.8 | 7.0 | 0.82 | 0.13 | 0.7 |
| 160 | 62.8 | 22.7 | 2.79 | 0.49 | 2.7 |
| 200 | 44.0 | 43.4 | 4.92 | 0.77 | 5.8 |
| 240 | 26.5 | 58.2 | 6.05 | 0.88 | 8.9 |
| 280 | 16.3 | 67.2 | 6.37 | 0.89 | 12.4 |

COMPARATIVE EXAMPLE C

Example III was essentially repeated except that no diatomaceous earth or other support was employed. The analytical results are shown below.

| Time  | Mols × 100 | | | | |
|-------|---------|------|------|------|------|
| (min.) | Toluene | IBB | NBB | MI | MP |
| 90 | 100 | 0 | 0 | 0 | 0 |
| 160 | 97.5 | 1.2 | 0.15 | 0 | 0.1 |
| 200 | 92.9 | 2.7 | 0.34 | 0 | 0.3 |
| 240 | 88.4 | 5.7 | 0.71 | 0.03 | 0.5 |

COMPARATIVE EXAMPLE D

A suitable reaction vessel was charged with 92 g of toluene, 4.9 g of −325 mesh potassium carbonate, 1.0 g of NaK, and $C_{11}$ paraffin as an internal standard. The mixture was heated to 185° C. with stirring, and propene was fed to a pressure of 2758 kPa, a pressure that was maintained. Samples were taken periodically and the reaction was then stopped as in Comparative Example A. The analytical results are shown below.

| Time  | Mols × 100 | | | | |
|-------|---------|------|------|------|------|
| (min.) | Toluene | IBB | NBB | MI | MP |
| 0 | 100 | 0 | 0 | 0 | 0 |
| 120 | 95.2 | 2.2 | 0.25 | 0.06 | 0.4 |
| 160 | 87.1 | 10.4 | 0.97 | 0.56 | 1.3 |
| 200 | 70.7 | 22.9 | 1.93 | 1.16 | 3.3 |
| 240 | 70.5 | 23.5 | 1.84 | 1.43 | 3.0 |
| 280 | 67.4 | 26.6 | 1.97 | 1.69 | 3.8 |

EXAMPLE IV

Comparative Example D was repeated except that 0.26 g of −325 mesh sodium hydroxide was included in the initial charge to the reaction vessel. The analytical results are shown below.

| Time  | Mols × 100 | | | | |
|-------|---------|------|------|------|------|
| (min.) | Toluene | IBB | NBB | MI | MP |
| 0 | 100 | 0 | 0 | 0 | 0 |
| 120 | 94.9 | 1.2 | 0.16 | 0.01 | 0.1 |
| 200 | 81.3 | 12.9 | 1.79 | 0.13 | 1.6 |
| 240 | 65.5 | 26.1 | 3.62 | 0.19 | 3.2 |
| 280 | 48.8 | 39.2 | 5.38 | 0.22 | 5.1 |
| 320 | 36.2 | 51.2 | 6.76 | 0.18 | 8.0 |

COMPARATIVE EXAMPLE E

Part A

A suitable reaction vessel was charged with 92 g of toluene, 1.1 g of potassium, and $C_{11}$ paraffin as an internal standard. The mixture was heated at 190° C. for one hour, after which the temperature was lowered to 185° C. with stirring, and propene was fed to a pressure of 2758 kPa, a pressure that was maintained. Samples were taken periodically and the reaction was then stopped as in Comparative Example A. The analyses made after 240 minutes of reaction time showed that only 34% of the toluene had been converted.

Part B

Part A was repeated except that 4.9 g of diatomaceous earth was included in the initial charge to the reaction vessel. The analyses made after 240 minutes of reaction time showed that 55% of the toluene had been converted—a 61.8% increase over the reaction rate obtained in the absence of a support.

Part C

Part A was repeated except that 2.9 mmols of water was included in the initial charge as a 565 ppm solution in toluene, and an extra 0.1 g of potassium was included to compensate for the amount that would react with the water to form potassium hydroxide. The analyses made after 240 minutes of reaction time showed that only 31% of the toluene had been converted—an 8.8% decrease in reaction rate.

EXAMPLE V

Comparative Example E, Part A, was repeated except that both 4.9 g of diatomaceous earth and 2.9 mmols of water (incorporated as a 565 ppm solution in toluene) were included in the initial charge, and an extra 0.1 g of potassium was included to compensate for the amount that would react with the water to form potassium hydroxide. The analyses made after 240 minutes of reaction time showed that 83% of the toluene had been converted—a 144.1% increase over the reaction rate obtained in the absence of either a support or a co-catalyst.

It is obvious that many variations may be made in the products and processes set forth above without departing from the spirit and scope of this invention.

What is claimed is:

1. In a process for coupling an alkene selected from ethene, propene, and mixtures thereof with an aromatic hydrocarbon having an active hydrogen on a saturated alpha-carbon in the presence of a supported potassium or potassium alloy as a catalyst, the improvement which comprises conducting the reaction in the presence of sodium hydroxide, potassium hydroxide, or a mixture thereof as a co-catalyst, the catalyst composition containing about 200–1500 weight % of support and about 4–40 mol % of co-catalyst, based on the amount of alkali metal catalyst.

2. The process of claim 1 wherein the alkene is a mixture of propene and ethene.

3. The process of claim 1 wherein the alkene is propene.

4. The process of claim 1 wherein the aromatic hydrocarbon is a hydrocarbon corresponding to the formula RR'R"CH, in which R is an aryl group of up to 20 carbons and R' and R" are independently selected from hydrogen and alkyl and aryl groups of up to 20 carbons.

5. The process of claim 4 wherein the aromatic hydrocarbon is an alkylbenzene.

6. The process of claim 5 wherein the alkylbenzene is toluene.

7. The process of claim 1 wherein the alkali metal is potassium.

8. The process of claim 1 wherein the alkali metal is a sodium-potassium alloy having a potassium content of 40-90% by weight.

9. The process of claim 1 wherein the co-catalyst is a preformed hydroxide or mixture of hydroxides.

10. The process of claim 1 wherein the co-catalyst is a hydroxide or hydroxide mixture formed in situ by adding water to a reaction mixture containing the supported catalyst.

11. The process of claim 1 which is conducted at a temperature of about 100°-300° C.

12. The process of claim 11 wherein the reaction temperature is about 175°-200° C.

13. The process of claim 1 wherein the support is diatomaceous earth.

14. The process of claim 1 wherein the support is potassium carbonate.

15. The process of claim 1 wherein the support is alumina.

16. The process of claim 1 wherein propene is coupled with toluene at about 175°-200° C. in the presence of a supported potassium or sodium-potassium catalyst and a co-catalyst formed in situ by adding water to the catalyst prior to contacting the reactants.

* * * * *